US007852469B1

(12) United States Patent
Sickenberger et al.

(10) Patent No.: US 7,852,469 B1
(45) Date of Patent: Dec. 14, 2010

(54) PARTICLE DETECTOR

(75) Inventors: David W. Sickenberger, Bel Air, MD (US); Virginia E. Foot, Salisbury (GB); Dean Payne, Salisbury (GB)

(73) Assignee: The United States of America as represented by the Secretary of the Army, Washington, DC (US)

( * ) Notice: Subject to any disclaimer, the term of this patent is extended or adjusted under 35 U.S.C. 154(b) by 542 days.

(21) Appl. No.: 11/867,190

(22) Filed: Oct. 4, 2007

(51) Int. Cl.
*G02B 27/32* (2006.01)

(52) U.S. Cl. ....................... 356/256; 356/432; 356/439; 250/461.1; 250/492.1; 250/288

(58) Field of Classification Search ................. 356/256, 356/432, 436–439; 250/461.2, 573–575, 250/461.1, 492.1, 458.1, 288
See application file for complete search history.

(56) References Cited

U.S. PATENT DOCUMENTS 7,201,878 B2 * 4/2007 Lin et al. .................... 250/288
7,532,320 B2 * 5/2009 Neiss et al. ................. 356/301

OTHER PUBLICATIONS

Davitt, K.., et al "Spectroscopic Sorting of Aerosols by a Compact Sensor Employing UV LEDs" Aerosol Science and Technology, 40:1047-1051, 2006.

* cited by examiner

*Primary Examiner*—Gregory J Toatley
*Assistant Examiner*—Iyabo S Alli
(74) *Attorney, Agent, or Firm*—Ulysses John Biffoni

(57) ABSTRACT

A particle detection device and method wherein a bulk sample of particles is selectively collected based on scattering properties of the particles and fluorescence properties of the particles. The bulk sample of particles is then excited to produce an atomic emission from the bulk sample of particles. The atomic emission from the bulk sample of particles is used to determine atomic emission properties of the particles and identify biological particles in the bulk sample.

24 Claims, 1 Drawing Sheet

PARTICLE DETECTOR

GOVERNMENT INTEREST

The invention described herein may be manufactured, licensed, and used by or for the U.S. Government.

TECHNICAL FIELD

The present invention relates to particle detectors, and, in particular, to particle detectors that combine radiation scattering, particle fluorescence, and atomic emissions.

BACKGROUND

Particle detectors, such as portable detectors, may use optical methods in the detection of aerosols within fluid samples. Optical methods are useful in detecting potentially harmful aerosols, such as biological aerosols that may be present after a biological agent attack or industrial accident. Biological molecules fluoresce when excited by ultraviolet (UV) radiation. As a result, biological molecules in an aerosol sample can be optically detected by irradiating the sample with ultraviolet radiation, and observing the fluorescence response. Since differing excitation wavelengths may be used to detect different classes of biological molecules, the excitation wavelength can be chosen to detect specific classes of biological molecules such as proteins, flavinoids, and metabolite products. However, detection methods that rely upon observing the fluorescence responses are susceptible to false positives in that certain non-biological molecules produce fluorescence responses when irradiated by ultraviolet radiation that are similar to fluorescence responses of biological molecules. This makes it difficult to determine whether an aerosol is harmful or not.

Another way of determining whether an aerosol is a biological aerosol is to obtain an atomic emission from the aerosol, e.g., using laser-induced breakdown spectroscopy. The atomic emission is then detected with an optical detector. An electronic signal produced by the optical detector in response to the atomic emission is analyzed, e.g., to determine whether inorganic materials, such as calcium, sodium, potassium, magnesium, etc., that are typically found in manufactured biological agents are present. This method, when coupled to fluorescence methods, is less susceptible to false positives than fluorescence only methods. However, this method requires expensive, power-intensive lasers and complex and expensive optical systems.

SUMMARY

An embodiment of the disclosure provides a method of detecting particles that includes selectively collecting a bulk sample of the particles based on scattering properties of the particles and fluorescence properties of the particles, exciting the bulk sample of particles to produce an atomic emission from the bulk sample of particles, and determining atomic emission properties of the particles of the bulk sample from the atomic emission from the bulk sample of particles.

DETAILED DESCRIPTION

Figure 1:
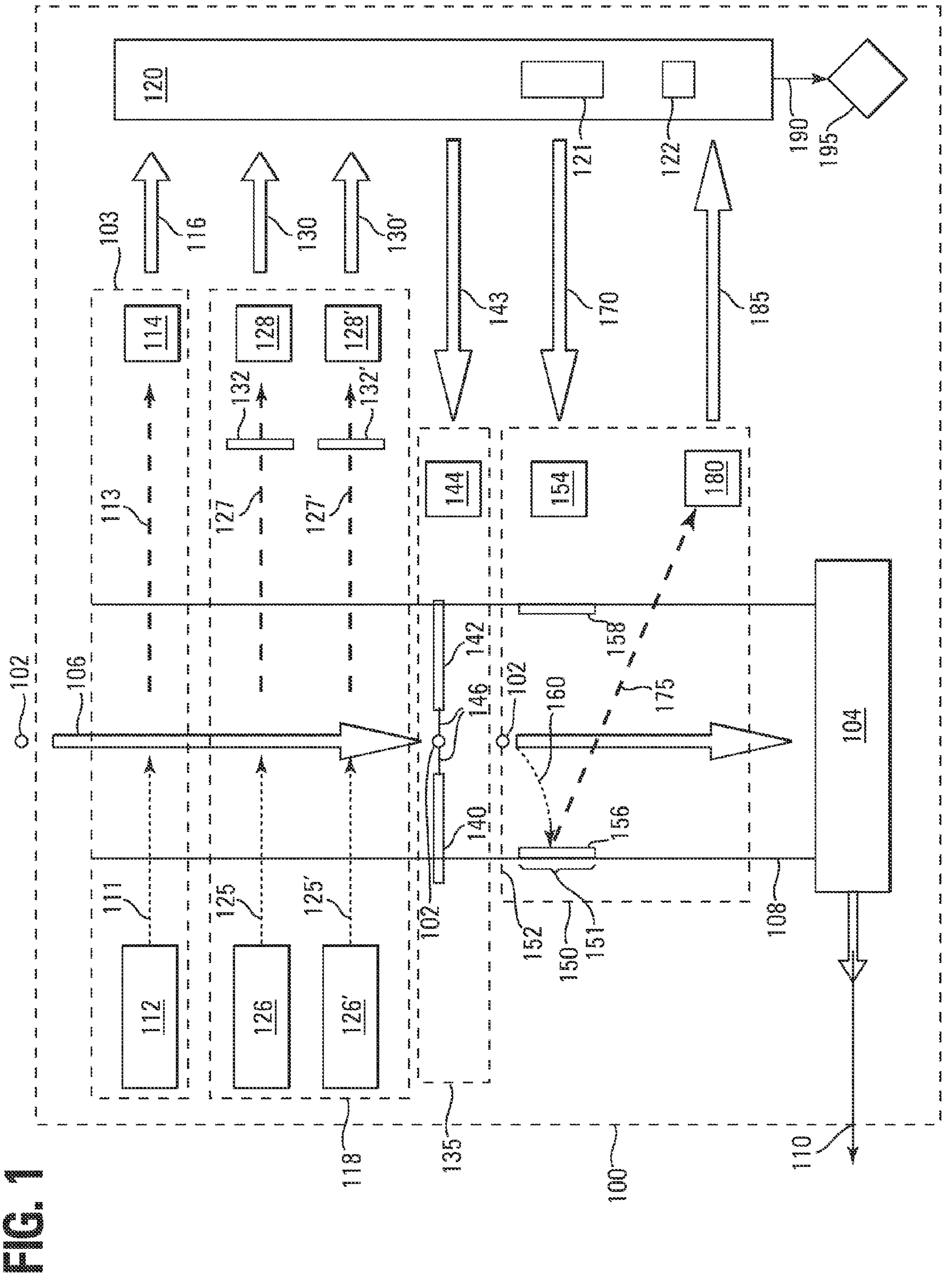
FIG. 1 is a block diagram illustration of an embodiment of a particle detector, according to an embodiment of the disclosure.

In the following detailed description, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice these embodiments. Other embodiments may be utilized and structural, logical, and electrical changes may be made without departing from the scope of the present disclosure.

FIG. 1 is a block diagram illustrating a particle detector 100, according to an embodiment. Particle detector 100 may be portable for use in the field. In operation, according to another embodiment, aerosol particles 102 (particles contained within a gas flow, such as air) are drawn to the detector 100, e.g., by a blower or an air pump 104 operating in a suction mode, as shown in FIG. 1. In FIG. 1, the trajectory of all sampled aerosol particles is represented by an arrow 106. For one embodiment, a housing 108 contains the flow of aerosol particles 102. Housing 108 may be of a material that is transparent or substantially transparent to radiation in the ultraviolet range, e.g., ultraviolet light, and radiation in the visible range, e.g., visible light, such as clear glass, clear plastic, or the like. Alternatively, non-transparent materials with clear ports to pass the ultraviolet and visible light may be used. The flow of aerosol particles 102 exits air pump 104 and is exhausted from particle detector 100 at an outlet 110.

For one embodiment, particle detector 100 includes a radiation scattering section 103 configured to determine radiation scattering properties of the particles 102. Particle detector 100 also includes a particle fluorescence section 118 configured to determine fluorescence properties of the particles 102. A particle selection section 135 is also included. Particle detector 100 includes an atomic emission section 150 configured to determine atomic emission properties of a bulk sample of particles 102 selected by particle selection section 135 based on the radiation scattering properties of the particles determined by radiation scattering section 103 and the fluorescence properties of the particles determined by the particle fluorescence section 118. For another embodiment, radiation scattering section 103, particle fluorescence section 118, particle selection section 135, and atomic emission section 150 are each coupled to a controller 120 of particle detector 100 configured to cause particle detector 100 to perform the methods of the various embodiments discussed below.

For one embodiment, as particles 102 flow toward pump 104, particles 102 enter radiation scattering section 103, where particles 102 can be irradiated by radiation 111, e.g., having a wavelength from about 800 to about 1200 nanometers, emitted by a radiation source 112, such as a laser that may be operated in a continuous mode, of radiation scattering section 103. When radiation 111 hits a particle 102, scattered light 113 is produced from particle 102. Scattered light 113, in the form of excitation photons, travels to an optical detector 114 of radiation scattering section 103 that detects scattered light 113. Detector 114 produces an electrical signal 116, e.g., an electrical current or voltage, in response to the photons impacting the detector 114. Electrical signal 116 is transmitted to controller 120 that has a processor 121, e.g., a computer. For one embodiment, controller 120 may digitize signal 116 and record and analyze the digitized signal 116. For one embodiment, controller 120 performs methods of various embodiments of the disclosure, as described below, in response to computer-readable instructions, e.g., contained on a computer usable medium 122.

Based on digitized signal 116 corresponding to the light 113 scattered from particle 102, controller 120 may determine the size and/or shape of particle 102, e.g., using methods that are known to those of skill in the art. The size and/or shape of particle 102 may be compared to historical size and/or shape data, such as historical size and/or shape data for certain particles, such as particles or molecules of certain biological agents. For one embodiment, statistical distributions of the size and/or shape of particles 102 may be obtained from the scattering data contained in electrical signal 116 and compared to historical distributions of the size and/or shape for the particles of biological aerosols.

When the size and/or shape of a particle 102 substantially matches the size and/or shape of particles of a certain biological agent (or aerosol) or the statistical distributions of the size and/or shape of particles 102 substantially matches a historical size and/or shape distribution, then particles 102 are determined to at least be potentially a particle of a biological aerosol. For example, the aerosol containing particles 102 is determined to be at least a biological threat. For example, when a difference between the size of a particle 102 and a particle of a biological agent is within a certain range (i.e., a predetermined amount), particle 102 is determined to at least be potentially a particle of a biological aerosol, i.e., at least a threat. Note that the size and/or shape determination via scattering is susceptible to false positives in that the particles of non-biological aerosols (e.g., non-biological threats) can have sizes and/or shapes that substantially match those of biological aerosols.

As particles 102 continue to flow toward pump 104, particles 102 exit the radiation scattering section 103 and enter particle fluorescence section 118, where particles 102 can be irradiated (e.g., excited) by excitation radiation 125 in the near or deep ultra violet range, e.g., having a wavelength from about 266 to about 380 nanometers, emitted by a radiation source 126 of particle fluorescence section 118. For one embodiment, excitation radiation 125 is nominally about 365 nanometers. Radiation source 126 may be a laser, a light emitting diode, xenon arc lamp, etc.

The wavelengths emitted by radiation source 126 are known to generate fluorescence in biological aerosols. That is, when particle 102 is a particle of a biological aerosol, when radiation 125 hits particle 102, particle 102 fluoresces, producing a fluorescence emission 127 at a longer wavelength than radiation 125. Fluorescence emission 127 can have a wavelength anywhere from about 10 nanometers to about a few hundred nanometers, e.g., about 400 to about 700 nanometers when radiation 125 has a nominal wavelength of about 365 nanometers. An optical detector 128 of particle fluorescence section 118 detects fluorescence emission 127, in the form of fluorescence emission photons, and outputs an electrical signal 130, e.g. a voltage or current signal, in response to detecting fluorescence emission 127, to controller 120.

For one embodiment, controller 120 may digitize signal 130 and record, process, and analyze the digitized signal 130. For one embodiment, a filter 132 is interposed between housing 108 and detector 128, e.g., in front of detector 128, to filter the photons of scattered light 113 from the photons of the fluorescence emission 127, thereby substantially preventing the photons of scattered light 113 from reaching detector 128.

Based on digitized signal 130, corresponding to the fluorescence emission 127 from particle 102, controller 120 may compare attributes of the fluorescence emission 127 to certain (e.g., predetermined) historical attributes of the fluorescence for certain biological aerosols. For example, spectra of the fluorescence emission 127 may be compared to historical fluorescence spectra for certain biological aerosols. When the attributes of the fluorescence emission 127, such as the spectra, substantially match the predetermined attributes of a certain biological aerosol, then particle 102 is determined to at least be potentially a particle of a biological aerosol. That is, the aerosol containing particles 102 is determined to be at least a biological threat. Note that a fluorescence analysis is susceptible to false positives in that the particles of non-biological aerosols (e.g., non-biological threats) can have fluorescence emissions that substantially match those of biological aerosols.

Based on the fact that multiple excitation wavelengths are known to be useful in providing discrimination information among biological and ambient aerosols, as particles 102 continue to flow toward pump 104, particles 102 may be irradiated (e.g., excited) by one or more additional frequencies of excitation radiation within particle fluorescence section 118 that are different from radiation 125. For example, particles 102 may be excited by excitation radiation 125' from a radiation source 126', e.g., similar to radiation source 126, of particle fluorescence section 118 having a nominal wavelength of about 280 nanometers when excitation radiation 125 has a nominal wavelength of about 365 nanometers. When particle 102 is a particle of a biological aerosol, when radiation 125' hits particle 102, particle 102 fluoresces, generating a fluorescence emission 127', e.g., at a wavelength of about 300 to about 700 nanometers when excitation radiation 125' has a nominal wavelength of about 280 nanometers.

An optical detector 128' of particle fluorescence section 118 detects fluorescence emission 127', in the form of fluorescence emission photons, and outputs an electrical signal 130', e.g. a voltage or current signal, in response to detecting fluorescence emission 127', to controller 120. For one embodiment, controller 120 may digitize signal 130' and record, process, and analyze the digitized signal 130'. For one embodiment, a filter 132' is interposed between housing 108 and detector 128', e.g., in front of detector 128', to filter the photons of scattered light 113 from the photons of the fluorescence emission 127', thereby substantially preventing the photons of scattered light 113 from reaching detector 128'.

Based on digitized signal 130', corresponding to the fluorescence emission 127' from particle 102, controller 120 may compare attributes of the fluorescence emission 127' to certain (e.g., predetermined) historical attributes of the fluorescence for certain biological aerosols. For example, spectra of the fluorescence emission 127' may be compared to historical fluorescence spectra for certain biological aerosols. When the attributes of the fluorescence emission 127', such as the spectra, substantially match the predetermined attributes of a certain biological aerosol, then particle 102 is determined to at least be potentially a particle of a biological aerosol. That is, the aerosol containing particles 102 is determined to be at least a biological threat. However, as described above, the biological threat could be a false positive in that the aerosol containing particles 102 could be a non-biological aerosol and thus a non-biological threat.

Note that radiation source 126', optical detector 128', and filter 132' are located downstream, e.g., on the order of millimeters, from radiation source 126, optical detector 128, and filter 132. This placement ensures that excitation radiation 125 and excitation radiation 125' do not overlap each other and that fluorescence emission 127 and fluorescence emission 127' do not overlap each other. In the event of an overlap, it would be nearly impossible to determine which radiation source, radiation source 126 or radiation source 126', produced fluorescence emission 127 or fluorescence emission 127'.

As indicated above, scattering information (or data) contained in electrical signal 116 and fluorescence information (or data) contained in electrical signals 130 and 130' provide information about the biological content of the aerosol of particles 102 passing through the detector. The scattering information and fluorescence information enables the determination of scattering and fluorescence properties of the aerosol of particles 102 that are compared to historical scattering and fluorescence properties for certain biological aerosols. When the thus determined scattering and fluorescence properties of the aerosol of particles 102 substantially match historical scattering information and/or the fluorescence information for biological aerosols, then particles 102 are defined as threat particles and the aerosol of threat particles 102 is defined as a threat aerosol.

Optical detectors 114, 128, and 128' can also be used to determine the velocity of the particles 102. For one embodiment, the velocity of the particles may be determined from elapsed times between the particle detections at the respective optical detectors and the known distances between the respective optical detectors. For one embodiment, controller 120 determines when particles 102 are located between opposing electrodes 140 and 142 of particle selection section 135, as shown in FIG. 1, based on the velocity of particles 102, the distance from the last optical detector making a detection, e.g., optical detector 128', and electrodes 140 and 142, and the elapsed time since the last optical detector made a detection.

Opposing electrodes 140 and 142 are each electrically coupled to an electrical power source 144, such as a DC power source, of particle selection section 135. For one embodiment, when controller 120 determines that particles 102 are located between electrodes 140 and 142, power source 144 selectively applies a voltage to each of electrodes 140 and 142 in response to receiving a control signal 143 from controller 120 when controller 120 has determined that particles 102 are threat particles based on the analysis of the scattering data of signal 116 and the analysis of the fluorescence data of at least one of signals 130 and 130'. That is, control signal 143 instructs power source 144 to apply the voltage to each of electrodes 140 and 142. However, in the event that the analysis of the scattering data and the analysis of the fluorescence data indicates that particles 102 are non-biological (e.g., non-threat) particles, controller 120 does not instruct power source 144 to apply a voltage to each of electrodes 140 and 142, e.g., by not sending a control signal to power source 144. That is, when no threat particles are detected, power source 144 does not apply a voltage to each of electrodes 140 and 142 when the particles are between electrodes 140 and 142.

Particles that are located between electrodes 140 and 142 are ionized by a corona discharge 146 generated by an electric field produced between electrodes 140 and 142 by the application of a voltage from power source 144. The electric field produced between the electrodes forms ions according to processes understood by those of skill in the art. As a result, particles 102 become electrically charged. Therefore, controller 120 decides whether or not to ionize particles 102 based on the scattering and fluorescence properties of particles 102. Several alternative ionization techniques exist, including radioactive, photo-ionization, and field ionization.

After passing between electrodes 140 and 142, particles 102 exit particle selection section 135 and enter atomic emission section 150 that includes a spark ionization section 151. Entry into atomic emission section 150 is shown at 152. Spark ionization section 151 includes a power source 154 and field plates 156 and 158. For one embodiment, a spark plug, e.g., of the type used in internal combustion engines, may provide field plates 156 and 158, where field plates 156 and 158 are respectively the electrodes of the spark plug.

During operation of detector 100, power source 154 applies a first voltage to field plates 156 and 158 that positively charges one of plates 156 and 158 and negatively charges the other of plates 156 and 158. When particles 102 are determined to be non-threat particles and are thus not charged between electrodes 140 and 142, the uncharged non-threat particles 102 pass through atomic emission section 150, flow through the pump 104, and are exhausted through outlet 110.

When particles 102 are determined to be threat particles and are thus charged between electrodes 140 and 142, the charged threat particles 102 migrate toward the one of plates 156 and 158 having the opposite charge under the influence of the electrostatic charge produced between plates 156 and 158. The migration of a particle 102 is exemplified by an example trajectory 160 in FIG. 1. The attractive force between the particles and the plates 156 and 158 due to the unlike charges of the particles and the plates 156 and 158 acts to adhere the particles to the respective plates.

Controller 120 can determine when a particle 102 enters atomic emission section 150 shown at 152 from the above-determined particle velocity and the known distance from electrodes 140 and 142 to the entry location 152. Controller 120 can also determine the speed at which a particle 102 travels in the electric field between plates 156 and 158 based on the mobility constant of that particle 102. Controller 120 can then determine the actual time it takes the particle 102 to travel within the field from entry point 152 until that particle 102 impacts a plate 156 or 158 based on the particle's initial position within the field, e.g., entry point 152, the total amount of charge on the particle, the ability of the particle to move in air at atmospheric pressure, the distance between the plates 156 and 158, and the voltage applied. In this way, controller can determine when the particle 102 arrives at the plate.

The air flow, applied voltages, the distance between the field plates 156 and 158, and ionization conditions, are adjusted so that the charged particles impact the field plates. The process can be extended to allow multiple particles to impact and adhere to the plates over various periods of time. For example, particles may be collected on field plate 156 and/or field plate 158 for a certain (e.g., predetermined) time interval, e.g., of about a minute. That is, the particles are allowed to collect for the certain time interval after it is determined that particles have started to collect on field plate 156 and/or field plate 158. This produces a bulk sample of particles 102 on field plate 156 and/or field plate 158.

Note that the bulk sample collected on field plate 156 and/or field plate 158 contains substantially all particles 102 that have been determined to be threat particles based on the scattering and fluorescence properties of these particles. That is, detector 100 can selectively collect bulk samples of threat particles based on the based on the scattering and fluorescence properties of these particles. This substantially reduces the number of non-threat potential particles in the sample in that, as described above, the non-threat particles are selectively exhausted without being collected on either of the field plates based on the scattering and fluorescence properties of these particles.

For one embodiment, electrodes 140 and 142 may be replaced by tubes, for example, for providing air jets that can selectively blow threat particles onto the field plates in response to control signal 143. For example, control signal 143 selectively activates the air jets, e.g., via a solenoid or the like, when controller 120 has determined that particles 102 that are aligned with the tubes are threat particles. The threat particles subsequently adhere to the field plates due to impaction, e.g., according to the same basic principle that causes particles to adhere in air filters.

The voltage output of power source 154 may be increased to a second voltage that is higher than the first voltage to produce electrostatic fields between field plates 156 and 158, e.g., in values above 1 million volts/meter. At these field strengths, the air between the field plates becomes ionized, resulting in a high-voltage spark across the gap between field plates 156 and 158. For one embodiment, the voltage output of power source 154 may be increased in response to receiving a control signal 170 at power source 154 from controller 120 when controller 120 has determined that particles 102 are threat particles based on the scattering properties the fluorescence properties of these particles. For example, control signal 170 instructs power source 154 to increase the voltage to field plates 156 and 158 when threat particles are collected on field plate 156 and/or field plate 158. For one embodiment, voltage output of power source 154 may be increased to a second voltage periodically, such as after each certain length of time, e.g., of about a minute, as described above. For example, controller 120 may transmit control signal 170 after the particles have collected on field plate 156 and/or field plate 158 for the certain length of time.

The energy from the spark excites the atoms of the bulk sample that has been selectively collected on field plate 156 and/or field plate 158. The result is an emission 175, e.g., of light, associated with the particles 102 constituting the bulk sample on field plate 156 and/or field plate 158. Such an emission is often called an atomic emission. Emission 175 travels from field plate 156 and/or field plate 158 to an optical detector 180 of atomic emission section 150. Optical detector 180 produces an electronic signal 185, containing information (or data), such as spectra, in response to the specific wavelengths produced from the different elemental emission wavelengths of interest. For one embodiment, multiple optical detectors 180 could be used to simultaneously collect spectra on several elements, where each of the optical detectors outputs an electrical signal 185. Each signal 185 is then transmitted to controller 120 for digitization and analysis. For one embodiment, controller 120 determines atomic emission properties from the information contained in the one or more signals 185.

While the drawing illustrates emissions for only plate 156, plate 158 would also have collected particles and would emit atomic emissions. Collection optics of atomic emission section 150 would direct emissions from both plates to one or more detectors 180.

As indicated above, the scattering and fluorescence properties provide an indication of a biological threat. As further indicated above, there is a potential for false positives in that some non-biological particles have scattering and/or fluorescence properties substantially the same as some biological particles. However, inorganic compounds, such sodium, potassium, magnesium, calcium, etc., are typically present in biological particles, but are not usually present in non-biological particles. Therefore, detecting the presence of inorganic compounds in a sample of threat particles is one way of confirming that the sample is likely a sample of biological particles. For one embodiment, then, controller 120 may determine whether or not the collected particles contain inorganic compounds, such sodium, potassium, magnesium, calcium, etc., based on the atomic emission properties of the particles of the bulk sample selectively collected on field plate 156 and/or field plate 158.

Note that selectively collecting a sample of threat particles on field plate 156 and/or field plate 158 based on the scattering and fluorescence properties of these particles reduces the non-biological ambient background signal that would otherwise be produced if non-biological were also included in the sample and thereby improves the sensitivity and discrimination of the atomic emission measurements. Moreover, obtaining atomic emission data from a selectively collected stationary bulk sample acts to reduce the power requirements and the component complexity associated with atomic emission methods that analyze the particles while they are in motion.

For one embodiment, in response to controller 120 determining that the atomic emission properties of the particles, based on data contained in the one or more data signals 185, are consistent with atomic emission properties of a known biological agent, controller 120 may set an alarm flag. For example, controller 120 may set an alarm flag in response to the atomic emission properties of the collected particles being consistent with the atomic emission properties of an inorganic compound typically found in a biological aerosol. For one embodiment, when the flag indicates a threat, due to the atomic emission properties of the collected particles being consistent with the atomic emission properties of a biological agent, and when the scattering and fluorescence properties of the collected particles indicate that a threat exists, controller 120 confirms a biological threat by generating an electrical signal 190 and transmits electrical signal 190 to a user interface 195, such as an audible alarm source, e.g., a horn, and/or a visual alarm source, e.g., an indicator light, indicative of a biological threat. In the event that the atomic emission data is not consistent with the threat, it is concluded that there is no threat, and no alarm is generated, regardless of whether the scattering and fluorescence properties indicate that a threat exists.

CONCLUSION

Although specific embodiments have been illustrated and described herein, it will be appreciated by those of ordinary skill in the art that any arrangement that is calculated to achieve the same purpose may be substituted for the specific embodiments shown. Many adaptations of the embodiments will be apparent to those of ordinary skill in the art. Accordingly, this application is intended to cover any adaptations or variations of the embodiments. It is manifestly intended that the embodiments be limited only by the following claims and equivalents thereof.

What is claimed is:

1. A particle detector comprising:

a radiation scattering section configured to determine radiation scattering properties of particles passing through the particle detector, a particle fluorescence section configured to determine fluorescence properties of the particles passing through the particle detector, a particle selection section; and an atomic emission section configured to determine atomic emission properties of a bulk sample of particles selected by the particle selection section based on the radiation scattering properties of the particles determined by the radiation scattering section and the fluorescence properties of the particles determined by the particle fluorescence section.

2. The particle detector of claim 1, wherein the atomic emission section is further configured to collect the bulk sample of particles.

3. The particle detector of claim 1, wherein the atomic emission section comprises a spark ionization section configured to produce a spark for exciting the bulk sample of particles to produce an atomic emission therefrom.

4. The particle detector of claim 3, wherein the atomic emission section further comprises an optical detector configured for detecting the atomic emission from the bulk sample.

5. The particle detector of claim 3, wherein the spark ionization section comprises a pair of plates electrically coupled to a power source.

6. The particle detector of claim 5, wherein the particle selection section includes a pair of electrodes configured to selectively electrically charge the particles of the bulk sample based on the radiation scattering properties of the particles determined by the radiation scattering section and the fluorescence properties of the particles determined by the particle fluorescence section.

7. The particle detector of claim 6, wherein the pair of plates is configured to collect the bulk sample thereon by attracting the selectively charged particles thereto.

8. The particle detector of claim 5, wherein the particle selection section is configured to selectively produce an air flow, based on the radiation scattering properties of the particles determined by the radiation scattering section and the fluorescence properties of the particles determined by the particle fluorescence section, for blowing the particles of the bulk sample onto at least one of the pair of plates.

9. The particle detector of claim 1, wherein the radiation scattering section comprises:

a radiation source that can produce radiation that can induce radiation scattering from the particles; and an optical detector that can detect radiation scattered by the particles.

10. The particle detector of claim 1, wherein the particle fluorescence section comprises:

one or more radiation sources that can produce radiation that can cause the particles to emit fluorescence; and an optical detector that can detect fluorescence emissions from the particles.

11. The particle detector of claim 1, wherein the bulk sample of particles is selected by said selection section when the radiation scattering properties and the fluorescence properties are consistent with radiation scattering properties and fluorescence properties of a biological agent.

12. A method for detecting particles, comprising:

selectively collecting a bulk sample of the particles based on scattering properties of the particles and fluorescence properties of the particles;

exciting the bulk sample of particles to produce an atomic emission from the bulk sample of particles; and determining atomic emission properties of the particles of the bulk sample of particles from the atomic emission from the bulk sample of particles.

13. The method of claim 12, wherein the scattering properties of the particles and the fluorescence properties of the particles respectively correspond to scattering properties and fluorescence properties of a biological material.

14. The method of claim 12, further comprising indicating a biological threat when the scattering properties of the particles and the fluorescence properties of the particles respectively correspond to scattering properties and fluorescence properties of a biological agent and when the atomic emission properties of the bulk sample of particles, correspond to atomic emission properties of a biological agent.

15. The method of claim 12, further comprising concluding that there is no biological threat when the atomic emission properties of the bulk sample of particles do not correspond to atomic emission properties of a biological agent, regardless of whether the scattering properties and the fluorescence properties of the particles respectively correspond to scattering properties and fluorescence properties of a biological agent.

16. The method of claim 12, wherein selectively collecting a bulk sample of the particles based on scattering properties of the particles and fluorescence properties of the particles further comprises charging the particles of the bulk sample based on the scattering properties of the particles and the fluorescence properties of the particles.

17. The method of claim 16, wherein selectively collecting the bulk sample of the particles based on the scattering properties of the particles and the fluorescence properties of the particles further comprises attracting the charged particles of the bulk sample to at least one plate of a pair of plates separated by a gap.

18. The method of claim 17, wherein exciting the bulk sample of particles to produce an atomic emission from the bulk sample of particles comprises exposing the bulk sample of particles on the at least one plate to a spark that is induced across the gap between the pair of plates.

19. A method of operating a particle detector, comprising;

drawing particles into the detector;

scattering radiation from the particles;

determining scattering properties of the particles from the scattered radiation;

generating fluorescence from the particles;

determining fluorescence properties of the particles from the generated fluorescence;

selectively collecting a bulk sample of the particles based on the determined scattering properties of the particles and the determined fluorescence properties of the particles;

producing an atomic emission from the bulk sample of the particles; and determining atomic emission properties of the particles of the bulks sample from the atomic emission.

20. The method of claim 19, further comprising determining that a biological threat exists when the determined scattering properties of the particles and the determined fluorescence properties of the particles respectively correspond to scattering properties and fluorescence properties of a biological agent and when the atomic emission properties of the particles correspond to atomic emission properties of a biological agent.

21. The method of claim 19, further comprising concluding that there is no biological threat when atomic emission properties of the particles do not correspond to atomic emission properties of a biological agent, regardless of whether the scattering properties and the fluorescence properties of the particles respectively correspond to scattering properties and fluorescence properties of a biological agent.

22. The method of claim 19, wherein producing the atomic emission from the bulk sample of the particles comprises exposing the bulk sample of the particles to a spark induced across a gap separating a pair of plates.

23. The method of claim 22, wherein selectively collecting the bulk sample of the particles based on the determined scattering properties of the particles and the determined fluorescence properties of the particles comprises:

selectively charging the particles of the bulk sample based on the determined scattering properties of the particles and the determined fluorescence properties of the particles; and attracting the charged particles to at least one of the pair of plates that has a charge opposite to the charged particles of the bulk sample.

24. The method of claim 22, wherein selectively collecting the bulk sample of the particles based on the determined scattering properties of the particles and the determined fluorescence properties of the particles comprises selectively blowing the particles of the bulk sample onto at least one of the pair of plates based on the determined scattering properties of the particles and the determined fluorescence properties of the particles.

* * * * *